US008377425B2

(12) United States Patent
Fleissman et al.

(10) Patent No.: US 8,377,425 B2
(45) Date of Patent: Feb. 19, 2013

(54) LONG WEARING COSMETIC COMPOSITIONS

(75) Inventors: Leona Giat Fleissman, Ridgewood, NJ (US); Sonal Pate, Jersey City, NJ (US); Maha Raouf, Franklin Lakes, NJ (US)

(73) Assignee: Avon Products, Inc., New York, NY (US)

( * ) Notice: Subject to any disclaimer, the term of this patent is extended or adjusted under 35 U.S.C. 154(b) by 1716 days.

(21) Appl. No.: 11/323,711

(22) Filed: Dec. 30, 2005

(65) Prior Publication Data

US 2007/0154440 A1 Jul. 5, 2007

(51) Int. Cl.
*A61Q 1/04* (2006.01)
*A61Q 1/00* (2006.01)

(52) U.S. Cl. .......................................... 424/64; 424/401

(58) Field of Classification Search ........................ None
See application file for complete search history.

(56) References Cited

U.S. PATENT DOCUMENTS

| | | | |
|---|---|---|---|
| 4,122,023 A | 10/1978 | Yasui et al. | |
| 4,832,944 A | 5/1989 | Socci et al. | |
| 4,847,071 A | 7/1989 | Bissett et al. | |
| 4,935,228 A | 6/1990 | Finkenaur et al. | |
| 5,318,775 A | 6/1994 | Shore et al. | |
| 5,340,569 A | 8/1994 | Elliott et al. | |
| 5,482,547 A | 1/1996 | Bugnon et al. | |
| 5,505,937 A | 4/1996 | Castrogiovanni et al. | |
| 5,747,017 A | 5/1998 | Nichols et al. | |
| 5,948,393 A | 9/1999 | Tomomasa et al. | |
| 6,027,739 A * | 2/2000 | Nichols .......................... | 424/401 |
| 6,120,753 A * | 9/2000 | Vinski et al. ..................... | 424/47 |
| 6,166,093 A | 12/2000 | Mougin et al. | |
| 6,258,348 B1 * | 7/2001 | Tsivkin ......................... | 424/70.12 |
| 6,261,576 B1 | 7/2001 | Fishman | |
| 6,277,386 B1 * | 8/2001 | Kim et al. ........................ | 424/401 |
| 6,309,629 B1 | 10/2001 | Travkina et al. | |
| 6,312,672 B1 | 11/2001 | Coolbaugh et al. | |
| 6,319,959 B1 * | 11/2001 | Mougin et al. ............... | 514/772.1 |
| 6,428,797 B2 | 8/2002 | Fishman | |
| 6,471,950 B1 | 10/2002 | Farer et al. | |
| 6,471,983 B1 | 10/2002 | Veeger et al. | |
| 6,482,397 B1 | 11/2002 | Scott et al. | |
| 6,509,009 B2 | 1/2003 | Nichols et al. | |
| 6,551,603 B1 | 4/2003 | Vinski et al. | |
| 6,627,724 B2 * | 9/2003 | Meijs et al. ........................ | 528/26 |
| 6,897,281 B2 * | 5/2005 | Lubnin et al. ..................... | 528/44 |
| 7,749,524 B2 | 7/2010 | Lu et al. | |
| 8,128,919 B2 * | 3/2012 | Fleissman et al. .......... | 424/78.03 |
| 2002/0159960 A1 | 10/2002 | Scancarella et al. | |
| 2003/0040571 A1 * | 2/2003 | Feng et al. ..................... | 524/837 |
| 2004/0191197 A1 | 9/2004 | Maio et al. | |
| 2004/0197298 A1 * | 10/2004 | Omura et al. ............ | 424/70.122 |
| 2005/0238611 A1 * | 10/2005 | Rando et al. ............. | 424/70.122 |
| 2006/0228315 A1 | 10/2006 | Fishman et al. | |

FOREIGN PATENT DOCUMENTS

| | | |
|---|---|---|
| EP | 0 602 905 A2 | 6/1994 |
| EP | 602905 B1 | 6/1994 |
| EP | 1588686 A1 | 10/2005 |
| JP | A-61-65809 | 4/1986 |
| JP | 07247312 A | 9/1995 |
| WO | 9963952 | 12/1999 |
| WO | 0007551 | 2/2000 |
| WO | 0239962 A1 | 5/2002 |
| WO | 2004054524 A1 | 7/2004 |
| WO | 2005/107683 A1 | 11/2005 |
| WO | 2005107683 A1 | 11/2005 |
| WO | 2006/113882 A1 | 10/2006 |

OTHER PUBLICATIONS

P. Bahadur et al., Principles of Polymer Science, p. 114, Table 3(h)(2005).*
Alzo, Bernal Personal Care Products, Dien inc. available at http://www.dieninc.com/html/partners/alzo.php (2006).*
International Search Report, PCT/US2006/047765.*

* cited by examiner

*Primary Examiner* — Jyothsna Venkat
(74) *Attorney, Agent, or Firm* — Charles S. Zeller; David M. Joyal; Joan M. McGillycuddy

(57) ABSTRACT

Cosmetic compositions comprising high molecular weight polyurethane polymers are disclosed. The polyurethane polymers typically will have a molecular weight greater than about 50,000. The cosmetic compositions provide cosmetic films on the lips which are comfortable, long-wearing, transfer-resistant, and have a shiny finish.

3 Claims, No Drawings

LONG WEARING COSMETIC COMPOSITIONS

FIELD OF INVENTION

The present invention relates generally to cosmetic compositions. More specifically, the invention relates to cosmetic compositions comprising high molecular weight polyurethane polymers that provide long-wearing and shine enhancing properties.

BACKGROUND OF THE INVENTION

It has long been considered desirable to provide cosmetic lip products, such as lipstick and lip gloss, which impart a shiny finish to the lips. Conventionally, cosmetic lip products comprise pigments dispersed in a base of fats or oils with various waxes added to provide the desired consistency of the product. However, the shiny finish provided by the conventional oily base comes at the cost of durability and transfer resistance.

Efforts to improve the durability and transfer resistance of cosmetic lip color products have focused on the use of polymeric film formers. For example, U.S. Pat. No. 5,505,937 discloses lipstick compositions comprising volatile solvents, silicone resins, wax, powder and oil which are said to be transfer resistant by the "Kiss test."

Patent Application No. JP-A-61-65809 discloses "transferless" lipstick compositions containing 1 to 70% by weight of a liquid silicone resin incorporating repeating silicate patterns (or having a three-dimensional lattice) comprising alkylated suspended chains of 1 to 6 atoms of carbon or phenylated chains, 10 to 98% by weight of a volatile silicone oil having a cyclic Si—O chain and containing methyl radicals, and pulverulent fillers.

Patent Application No. EP-A-602905 discloses "transferless" lipsticks containing a volatile cyclic or linear silicone containing suspended methylated chains and a silicone resin incorporating a suspended esterified chain having at least 12 atoms of carbon.

U.S. Pat. No. 6,309,629 discloses cosmetic compositions, such as lip gloss, which are smooth, glossy and wear resistant.

To date, efforts to provide transfer resistant lip product have met with only moderate success, however. Commercial transfer resistant lip products have been reported to be uncomfortable to wear and may have a drying effect on the lips. Further, the shiny finish which is sought in lip gloss products has not satisfactorily been replicated in transfer resistant products.

There is an ongoing need for cosmetic compositions, which may be used, for example, as lip gloss compositions, that combine high shine, fluidity, and smooth consistency with wear resistance and vibrant color. It is therefore an object of the present invention to provide cosmetic compositions, such as lipstick and lip gloss, which meet all of these requirements.

SUMMARY OF THE INVENTION

In accordance with the foregoing objectives and others, the present invention overcomes the deficiencies in the prior art by providing compositions and methods for forming long-wearing, shiny films on the body, including lips, skin, nail, and the like.

In one aspect of the invention, a cosmetic composition, such as, for example, a lip gloss, is provided comprising a film-forming polyurethane polymer having a weight average molecular weight of at least about 50,000, the polyurethane polymer being present in an effective amount to impart long lasting, shiny film when applied to a surface of the human body, such as the lips. In various implementations, the polyurethane polymer will have a weight average molecular weight of at least about 75,000, or at least about 100,000. The viscosity of the polyurethane polymer will typically range from about 130,000 to about 2,500,000 cps, preferably from about 400,000 to about 2,500,000 cps, and most preferably, from about 750,000 to about 2,500,000.

In one variant according to this aspect of the invention, the polyurethane polymer comprises the product of reaction between a diisocyanate and a diol, wherein the diol has of the form:

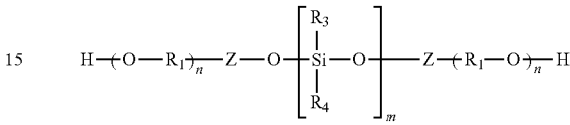

wherein,
$R_1$ represents, independently at each occurrence, and optionally substituted, branched or straight chain alkyl group having from two to ten carbon atoms;
n is an integer from 2 to about 200;
$R_3$ and $R_4$ are independently selected, at each occurrence, from the group consisting of optionally substituted, branched or straight chain $C_1$-$C_{10}$ alkyl, alkenyl, alkynyl, aryl, heteroaryl, alkyl-aryl, aryl-alkyl, alkoxy, amino, hydroxyl, hydrido, carboxy, cyano, and halogen;
m is an integer from 2 to about 5,000; and
Z represents a bond or a spacer group comprising from one to ten carbon atoms and optionally including one or more heteroatoms.

In particularly interesting implementations according to this aspect of the invention, the diisocyanate comprises isophorone diisocyanate. Preferred polyurethane polymers include bis-PEG-1 dimethicone-propylene glycol/IPDI copolymer, bis-PEG-1 dimethicone-dimer diol/IPDI copolymer, and bis-PEG-1 dimethicone-trimethylolpropane dioleate/IPDI copolymer.

In another aspect of the invention, a method is provided for forming a cosmetic film on a surface of the body, such as the lips, comprising applying thereto a composition comprising the polyurethane polymers described above in an effective amount to impart a long-wearing, shiny film on the surface.

These and other aspects of the present invention will become apparent to those skilled in the art after a reading of the following detailed description of the invention, including the illustrative embodiments and examples.

DETAILED DESCRIPTION OF THE INVENTION

All terms have their ordinary meaning in the art unless otherwise defined herein. As used herein, the term "diol" is intended to include any molecule have at least two hydroxyl groups available to react with diisocyante. The term "diol" does not exclude the possibility of additional hydroxyl groups also being present, and therefore specifically includes polyols and the like. The term "effective amount" refers to that amount of polyurethane polymer necessary to provide continuous film on the surface of the lips and preferably last for at least about two hours, more preferably at least about four hours, most preferably at least about six hours, and more preferred still at least about eight hours, under normal activity without the need for re-application. The "effective amount" will typically be about 0.1 to about 60% by weight, particularly from about 2 to about 40% by weight, and preferably from about 5 to about 20% by weight of the cosmetic product.

An essential component of the inventive cosmetic formulations is a high molecular weight, high viscosity polyurethane polymer which acts as a film former. In the broadest aspect of the invention, it is contemplated that any polyurethane polymer will be suitable. The polyurethane polymer will typically have a weight average molecular weight greater than about 50,000, preferably greater than about 75,000, and more preferably greater than about 100,000. The viscosity of the polyurethane polymer will typically range from about 130,000 to about 2,500,000 cps, preferably from about 400,000 to about 2,500,000 cps, and more preferably from about 750,000 to about 2,500,000 cps.

It has surprisingly been found that inclusion of these film-forming high molecular weight polyurethane polymers in cosmetic compositions provides films that are more comfortable, less tacky, longer-wearing, and have enhanced shine properties as compared to conventional film forming polymers.

The polyurethane polymers of the invention are typically obtained by the reaction of a diisocyanate component with a diol component according to methods well-known in the art. Suitable diisocyante and diol components are discussed below.

a. Diisocyanate Component

The diisocyanate will have the general form O=C=N—R—N=C=O where R represents an optionally substituted, branched or straight chain substituent comprising alkyl groups, aryl groups, or combinations of alkyl and aryl groups. R may therefore include alkyl, cycloalkyl, alkyl-cycloalkyl, aryl, alkyl-aryl, aryl-aryl, aryl-alkyl-aryl, and the like. Specific diisocyanates contemplated to be useful include, without limitation, toluene diisocyanate (TDI), methylene diphenyl diisocyanate (MDI), hexamethylene diisocyanate (HDI), 1,5-napthalene diisocyante (NDI), p-phenylene diiosocyanate (PPI), isophorone diisocyanate (IPDI), and the like. Isophorone diisocyante (IPDI), shown below, is the currently preferred diisocyanate for preparing the polyurethane polymers according to the invention.

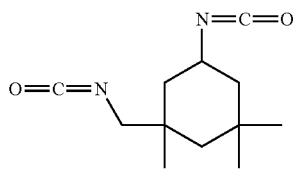 [SMILES: CC1(C)CC(N=C=O)CC(C)(CN=C=O)C1]

b. Diol Component

There is essentially no constraint on the selection of the diol component. The diol component will typically comprise a straight chain or branched spacer having hydroxyl functional groups at both terminal ends, optionally containing one or more unsaturated bonds and optionally containing one or more heteroatoms. The diol can be, for example, an alkyl diol, polyether polyol, polyester polyol, polyesteramide polyol, polythioether polyol, polycarbonate polyol, polyacetal polyol, polyolefin polyol, and the like.

Suitable alkyl diol, include without limitation, $C_3$ to $C_{30}$ alkyl diols such as, for example, 1,6-dihydroxyhexane, 1,7-dihryoxyheptane, 1,8-dihyroxyoctane, 1,9-dihydroxynonane, 1,10-dihydroxydecane, myristyl alcohol dimer, isocetyl alcohol dimer, isostearyl alcohol dimer, laureth-3 alcohol dimer, octyldodecyl alcohol dimer, and the like.

Suitable polyether diols include polyalkylene oxide diols of the form HO—$(R_1$—O$)_n$—H where $R_1$ represents a branched or straight chain alkyl group having from two to ten carbon atoms, preferable from two to three carbon atoms, and where n is an integer from 2 to about 200, preferably from 2 to about 100, and more preferably from about 2 to about 50. More preferably, the diol is of the form HO—$(CH_2CHR_2$—O$)_n$—H where $R_2$ represents H (polyethylene glycol, PEG) or $CH_3$ (polypropylene glycol, PPG). It is contemplated that random, alternating, and block copolymers of ethylene glycol and propylene glycol will also be useful.

The diol component may also comprise a polyester glycol, including, for example, products obtained by polycondensing aliphatic dicarboxylic acids with a glycol. Exemplary aliphatic dicarboxylic acids include succinic acid, malonic acid, glutaric acid, adipic acid, pimelic acid, suberic acid, azelaic acid, sebacic acid, dodecanedicarboxylic acid, and cyclohexanedicarboxylic acid. Glycols include, without limitation ethylene glycol, propylene glycol, 1,4-butanediol, 1,6-hexanediol, cyclohexane dimethanol, neopentylene glycol, pentaerythritol, polyether glycols, and the like.

The diol may also be an organosiloxane diol of the form:

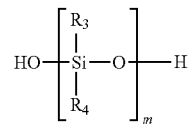

where m is an integer from 2 to about 5,000, preferably from 2 to about 2,500, and more preferably from about 2 to about 1,000; and where $R_3$ and $R_4$ are independently selected, at each occurrence, from the group consisting of substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, hydroxyl, hydrido, carboxy, cyano, or halogen. Preferably, $R_3$ and $R_4$ are independently selected from the group consisting of $C_1$-$C_6$ alkyl groups, and more preferably, $C_1$-$C_3$ alkyl groups in a currently preferred embodiment, at least one of $R_3$ and $R_4$ is methyl, and even more preferably, both $R_3$ and $R_4$ are methyl. In the case where both $R_3$ and $R_4$ are methyl, the organosiloxane polymer will be a polydimethylsiloxane, commonly known as a dimethicone.

The organosiloxane polymer may further comprise monomers having branching points of the T or Q type. When present, the T and Q structures will typically represent less than about 50%, preferably less than about 20%, and more preferably less than about 10% of the total repeat units in the organopolysiloxane polymer.

Other interesting diols may be prepared by the addition of polyalkylene oxide diols, such as PEG or PPG, to any of the foregoing diols. For example, hydroxy carboxylic acids, such as hydroxyl caproic acid, may be esterified with polyalkylene glycols to provide diols. Similarly, useful diols are obtained by transesterification of lactones such as butyrolactone and caprolactone with polyalkylene glycols.

Particular mention may be made of block copolymers of polyalkylene glycols, such as PEG, with the organosiloxane diols described above. In one such embodiment, the diol component is a copolymer of a first component having the form—$(R_1$—O$)_n$—H and a second component comprising a diol derived from an organosiloxane polymer. One exemplary copolymer has the form:

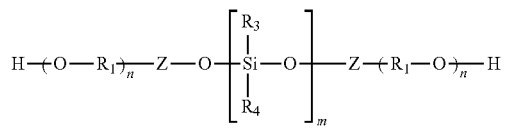

where n, m, $R_1$, $R_3$ and $R_4$ are defined as above, and wherein Z represents a bond or a spacer group comprising from one to ten carbon atoms and optionally including one or more heteroatoms. Preferably, Z is a group of the form:

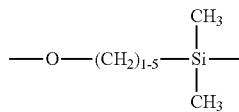

The copolymer is preferably of the form ABA where A represents the polyalkylene glycol component and B represents the polyorganosiloxane component, but may also be, for example, a copolymer of the form AB, BAB, ABAB, and the like. Such polymers will include those known in the art as bis-PEG-dimethicone diols.

In a particularly interesting variant, the bis-PEG-dimethicone diol will have the structure:

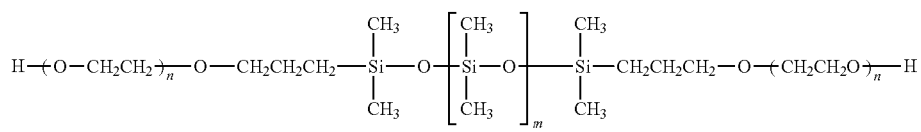

where m and n are as defined above. This compound has been assigned the Chemical Abstracts registry number CAS# 102783-01-7.

The urethane polymers according to the invention may also comprise mixtures of diols and mixtures of diisocyanates and may be block, alternating, or statistical copolymers.

C. Preferred Polyurethanes

The following structure is illustrative of the currently preferred polyurethane polymers according to the invention:

about 2,500,000 cps, preferably from about 400,000 to about 2,500,000 cps and most preferably, from about 750,000 to about 2,500,000 cps.

There is essentially no restriction on the selection of the terminal group X. X may be selected to modify one or more properties of the polymer, including lipophilicity, water solubility, tack, viscosity, and the like. Preferably, X will comprise a hydroxyl group or other functional group that is reactive with the isocyanate functionality. Therefore, X may represent, without limitation, an alcohol, a diol, or a polyol, including for example, any of diols described herein.

In one exemplary embodiment, X represents the polypropylene glycol, PPG-26. In the case where X is PPG-26, the polyurethane polymer has been given the proposed INCI name bis-PEG-1 dimethicone-polypropylene glycol-26/IPDI copolymer and is commercially available from Alzo International under the name Polyderm™ PPI-SI-G.

In another preferred embodiment, X is the dimer diol shown below:

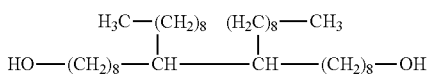

In the case where X represents a dimer diol, the polyurethane polymer has been given the proposed INCI name bis-PEG-1 dimethicone—dimer diol/IPDI copolymer and is commercially available from Alzo International under the name Polyderm™ PPI-SI-GD.

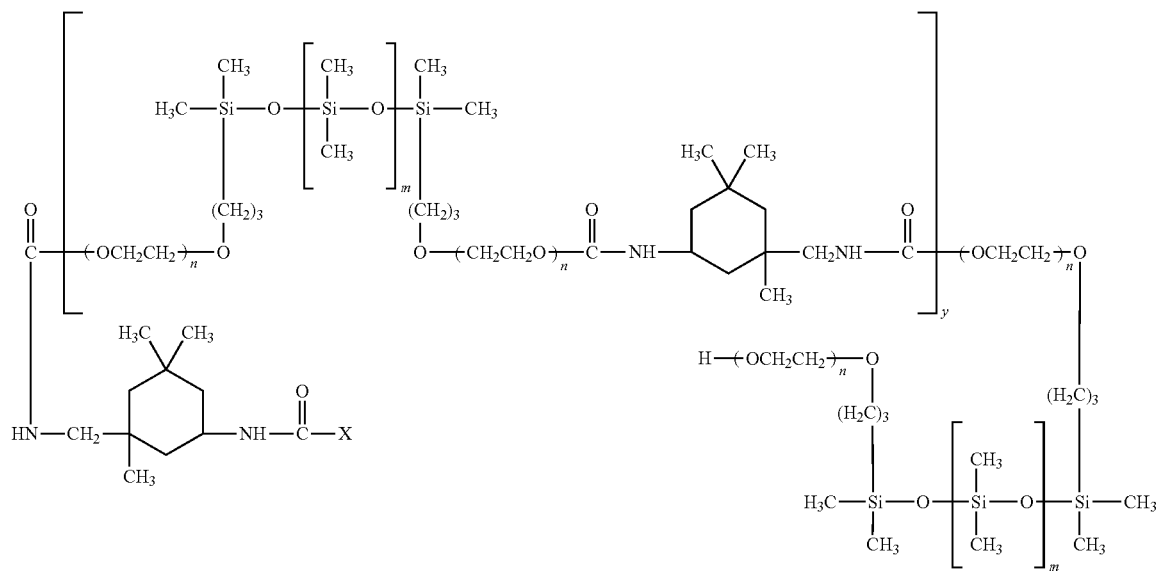

where n and m are as defined above, y represents the degree of polymerization, and X is a terminating group.

Y is selected to provide a polymer having a weight average molecular weight greater than about 50,000, preferably greater than about 75,000, and more preferably greater than about 100,000 and a viscosity ranging from about 130,000 to In yet another preferred embodiment, X represents trimethylolpropane dioleate, shown below:

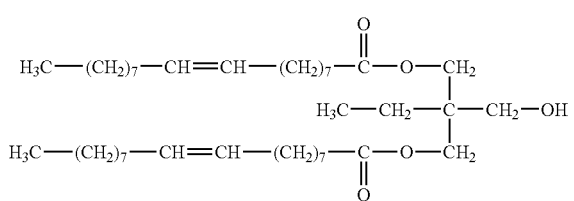

In this case, the polyurethane polymer has been given the proposed INCI name bis-PEG-1 dimethicone—trimethylolpropane dioleate/IPDI copolymer and is commercially available from Alzo International under the name Polyderm™ PPI-SI-DO.

d. Cosmetics

The high molecular weight polyurethane polymers may be incorporated into any cosmetic formulation. While the high molecular weight polyurethanes of the invention are ideally suited for lip products, nail enamels, and mascara because they impart enhanced shine properties in addition to the long-wearing benefits, it is contemplated that they will be useful in formulating other cosmetic compositions as well, including without limitation, foundation, eye shadow, blush and the like, where long-wearing properties are desired. It is within the skill in the art to formulate any such cosmetic product with the high molecular weight polyurethane polymers described herein.

The amount of these film-forming polyurethane polymers to be incorporated into the cosmetic formulations of the present invention is typically from about 0.1 to 60% by weight, particularly from about 2 to 40% by weight, and preferably from about 5 to about 20% by weight.

The cosmetic compositions are advantageously provided as one-part formulations, eliminating the need to apply overcoat layers. It is within the skill in the art formulate the high molecular weight polyurethanes of the invention into any conventional cosmetic product, including lipstick or lip gloss products. Lipsticks and lipcolors may be prepared, for example, by including the high molecular weight polyurethanes in place of conventional film-formers. Such conventional lip products include, without limitation, U.S. Pat. Nos. 6,509,009, 6,428,797, 6,261,576, 5,747,017, 5,318,775, and 4,935,228, the disclosures of which are hereby incorporated by reference.

The compositions will typically comprise one or more coloring agents. It is within the skill in the art to choose coloring agents and combinations of coloring agents to produce a desired color. Suitable coloring agents, including pigments, lakes, and dyes, are well known in the art and are disclosed in the C.T.F.A., International Cosmetic Ingredient Dictionary and Handbook, 10$^{th}$ Edition, 2004, the contents or which are hereby incorporated by reference. Organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-Fe$_2$O$_3$, y-Fe$_2$O$_3$, Fe$_3$O$_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, and the like. The colorants may be surface modified with, for example, fluoropolymers, to adjust one or more characteristics of the colorant as described in, for example, U.S. Pat. Nos. 6,471,950, 5,482,547, and 4,832,944, the contents of which are hereby incorporated by reference. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference. Other suitable pearlescent materials typically are pigments or layers of titanium dioxide on a substrate such as mica, polyethylene terephthalate, bismuth oxychloride, aluminum oxide, calcium borosilicate, synthetic flourophlogopite (synthetic mica), silica, acrylates copolymer, methyl methacrylate, and the like.

The coloring/pearling agents can represent from 0.1 to 50% and better still from 2 to 30% of the total weight of the composition.

The cosmetic compositions may further comprise one or more waxes, fats, and emollients to provide the desired body to the product. The fats may be natural animal and vegetable fats and oils, and semi-synthetic fats and oils, examples of which include avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, caster oil fatty acid methyl ester, sunflower oil, grape seed oil, bayberry wax, jojoba oil, macadamia nut oil, bees wax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, and egg yolk oil. Additionally, the term "POE" as used herein stands for polyoxyethylene.

The cosmetic compositions of the invention may optionally comprise other active and inactive ingredients, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfolients, lubricants, fragrances, colorants, staining agents, depigmenting agents, hypopigmenting agents, preservatives, stabilizers, pharmaceutical agents, photostabilizing agents, spherical powders and mixtures thereof. In addition to the foregoing, any other compound for the treatment of skin disorders may be included.

Specific examples of active and inactive ingredients contemplated to be useful include, without limitation, anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, amines (e.g., N, N-diethylhydroxylamine, aminoguanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, the contents of which are hereby incorporated by reference.

EXAMPLE 1

A long-wearing, shiny lip gloss is provided in Table 1.

| Ingredient | % (Weight) |
| --- | --- |
| Microcrystalline Petroleum Wax | 6.00 |
| Candelilla Wax | 1.38 |
| C30-45 Alkyl Methicone Wax | 1.00 |
| Ozokerite 170-D Wax | 0.68 |
| Micro Wax White | 0.55 |
| Bis-Peg-1 Dimethicone-Trimethylolpropane Dioleate/IPDI Copolymer (neat) (Alzo, Polyderm ™ PPI-SI-DO) | 11.00 |
| *Jojoba* Oil | 8.14 |
| Lanolin-Low Odor | 7.00 |
| Petrolatum | 5.00 |
| Stearyl PPG-3 Myristyl Ether Dimer Dilinoleate | 4.00 |
| Phenyl Trimethicone | 2.00 |
| Hydrolyzed Wheat Protein (moisturizer) | 0.60 |
| Cholesteryl BLO Glutamate (moisturizer) | 0.50 |
| *Aloe* Extract (moisturizer) | 0.25 |
| Tocopheryl Acetate-Syn (antioxidant) | 0.20 |
| Diphenyl Dimethicone | 14.00 |
| Methyl Trimethicone | 13.00 |
| Hydrogenated Polycyclopentadiene/Isododecane (Film Former) | 9.50 |
| Nylon Powder-Spherical | 2.00 |
| Acrylate Copolymer | 0.10 |
| Fragrance | 0.10 |
| Titanium Dioxide | 5.71 |
| Iron Oxides-Red | 2.90 |
| Brown Umber Oxide | 2.55 |
| Cosmetic Red Oxide | 0.68 |
| D&C Red No. 7 | 0.41 |
| Colorona Bordeaux | 0.75 |

EXAMPLE 2

Another long-wearing, shiny lip gloss formulation is provided in Table 2.

TABLE 2

| Ingredient | % (Weight) |
| --- | --- |
| Hydrogenated Polyisobutene/gellants/BHT | 46.62 |
| 60% w/w Bis-Peg-1 Dimethicone-Polypropylene Glycol-26/IPDI Copolymer in Isodecane (Alzo, Polyderm ™ PPI-SI-G) | 33.25 |
| Polybutene | 2.5 |
| Polyetheylene | 0.2 |
| Petrolatum | 1.9 |
| Diisostearyl Fumarate | 5.0 |
| Benzoic Acid | 0.1 |
| Mica | 1.24 |
| Titanium Dioxide | 2.3 |
| Cosmetic Red Oxide | 0.55 |
| Iron Oxide-Yellow | 0.55 |
| Iron Oxide Red | 2.8 |
| D&C Red No. 7 | 1.3 |
| Barium Sulfate | 1.36 |
| Ceramide in Soybean Oil | 1.00 |
| Fragrance | 0.20 |
| Vitamin Concentrate | 0.03 |
| Synthetic Wax | 0.10 |

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A cosmetic composition comprising a film-forming polyurethane polymer selected from the group consisting of bis-PEG-1 dimethicone-dimer diol/ isophorone diisocyanate copolymer and bis-PEG-1 dimethicone-trimethylolpropane dioleate/isophorone diisocyanate copolymer, wherein the film-forming polyurethane polymer is from about 0.1 to 60% of the weight of the composition.

2. A method for providing a cosmetic film on a human surface comprising applying thereto a cosmetic composition according to claim 1.

3. The cosmetic composition of claim 1 wherein the cosmetic composition is a lip composition.

\* \* \* \* \*